United States Patent
Pandey et al.

(10) Patent No.: US 8,609,837 B2
(45) Date of Patent: Dec. 17, 2013

(54) METALLATION ENHANCEMENTS IN TUMOR-IMAGING AND PDT THERAPY

(75) Inventors: Ravindra K. Pandey, E. Amherst, NY (US); Heinz Baumann, Buffalo, NY (US); Yihui Chen, Amherst, NY (US); Penny Joshi, Amherst, NY (US); Nayan Patel, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 124 days.

(21) Appl. No.: 13/168,421

(22) Filed: Jun. 24, 2011

(65) Prior Publication Data

US 2012/0097538 A1    Apr. 26, 2012

Related U.S. Application Data

(60) Provisional application No. 61/361,718, filed on Jul. 6, 2010.

(51) Int. Cl.
*C07D 487/22* (2006.01)
*G01N 33/559* (2006.01)

(52) U.S. Cl.
USPC .......................................... 540/145; 204/450

(58) Field of Classification Search
USPC .......................................... 540/145; 204/450
See application file for complete search history.

(56) References Cited

U.S. PATENT DOCUMENTS

| | | |
|---|---|---|
| 4,649,151 A | 3/1987 | Dougherty et al. |
| 4,866,168 A | 9/1989 | Dougherty et al. |
| 4,889,129 A | 12/1989 | Dougherty et al. |
| 4,932,934 A | 6/1990 | Dougherty et al. |
| 4,968,715 A | 11/1990 | Dougherty et al. |
| 5,002,962 A | 3/1991 | Pandey et al. |
| 5,015,463 A | 5/1991 | Dougherty et al. |
| 5,028,621 A | 7/1991 | Dougherty et al. |
| 5,145,863 A | 9/1992 | Dougherty et al. |
| 5,198,460 A | 3/1993 | Pandey et al. |
| 5,225,433 A | 7/1993 | Dougherty et al. |
| 5,314,905 A | 5/1994 | Pandey et al. |
| 5,459,159 A | 10/1995 | Pandey et al. |
| 5,498,710 A | 3/1996 | Pandey et al. |
| 5,591,847 A | 1/1997 | Pandey et al. |
| 2009/0043090 A1 * | 2/2009 | Pandey et al. ............... 540/135 |

OTHER PUBLICATIONS

Kee, Journal of Photochemistry and Photobiology A: Chemistry, vol. 200, No. 2-3, pp. 346-355 (2008).*
Liu et al. Cancer Research, vol. 64, pp. 6579-6587 (2004).*

* cited by examiner

*Primary Examiner* — Porfirio Nazario Gonzalez
(74) *Attorney, Agent, or Firm* — Michael L. Dunn

(57) ABSTRACT

A compound in the form of a metallized tetrpyrollic photosensizer linked to a fluorescent dye where the photosensitizer (PS), is linked by a structure that does not have detrimental radiation emmitance or absorbing characteristics, to a fluorophore, usually a cyanine dye (CD). The photosensitizer in accordance the invention is a metallized analog of porphyrins, chlorins, purpurinimides, bacterio pupurinimides, phthalocyanines, expanded porphyrins, benzoporphyrin derivatives and purpurins. The fluorophore is usually a cyanine dye with variable substituents. And, A method for determining effectiveness of PDT by comparing proportion of STAT-3 monomer with crosslinked STAT-3 dimer after PDT where the relative proportion of STAT-3 monomer to crosslinked STAT-3 directly correlates to efficacy of the PDT.

6 Claims, 3 Drawing Sheets

METALLATION ENHANCEMENTS IN TUMOR-IMAGING AND PDT THERAPY

CROSS-REFERENCE TO RELATED APPLICATIONS

This application claims the benefit under 35 U.S.C. §119(e) of U.S. Provisional Application No. 61/361,718, filed Jul. 6, 2010.

STATEMENT REGARDING FEDERALLY SPONSORED RESEARCH OR DEVELOPMENT

This invention was made with government support under CA055791 and CA127369 awarded by National Institutes of Health. The government has certain rights in the invention.

BACKGROUND OF THE INVENTION

A major challenge of cancer therapy is preferential destruction of malignant cells with sparing of the normal tissue. Critical for successful eradication of malignant disease are early detection and selective ablation of the malignancy. This proposal addresses both issues.

Multiple, complementary techniques for tumor detection, including magnetic resonance, scintigraphic and optical imaging are under active development, each approach has particular strengths and advantages. Optical imaging includes measurement of absorption of endogenous molecules (e.g. hemoglobin) or administered dyes, detection of bioluminescence in preclinical models, and detection of fluorescence from endogenous fluorophores or from targeted exogenous molecules. Fluorescence, which involves absorption of light and re-emission at a longer wavelength, can be highly sensitive: a typical cyanine dye with a lifetime of 0.6 nsec can emit up to $10^{32}$ photons/second/mole. A sensitive optical detector can image <$10^3$ photons/second. Thus even with low excitation power, low concentrations of fluorescent molecular beacons can be detected.

As with other non-invasive techniques, fluorescence imaging has the potential for performing in vivo diagnosis in situ, with real time display of the resulting information [46]. Optical tomographic techniques are being devised to visualize the fluorescent probes within tissue volumes. Optical imaging instruments may be simpler and less expensive to operate than those required for other imaging technologies, permitting their eventual application by less specialized medical centers. Therapeutically in applications such as endoscopic examination, fluorescence imaging can allow precise assessment of the location and size of a tumor, and provide information on its invasiveness. During debulking surgery, where malignant loci can be difficult to identify, the presence of a fluorescent signal might assist the surgeon in identifying the diseased site.

The optimal wavelength range for in vivo fluorescence excitation and emission is determined by tissue optical properties. Hemoglobin has strong absorption at wavelengths less than about 600 nm and there can be significant background fluorescence from endogenous biomolecules up to about 680 nm. At longer wavelengths into the near infrared (NIR), tissue absorption and scattering decrease with wavelength. As shown in FIG. 1 there is a large increase in light penetration as wavelengths increase from ~600 to 800 nm. In addition, the difference between the fluorophore's absorption and emission bands (i.e. its Stokes shift), should be at least 20 nm, to readily discriminate between the excitation and emission light. Many NIR fluorescent dyes are based on carbocyanine molecules such as indocyanine green (ICG), an FDA-approved agent with a 730 nm excitation and 830 nm emission maxima. Various novel ICG analogs have been evaluated because of the high biocompatibility and desirable spectral properties of the carbocyanines.

A challenge is to deliver the dyes selectively and in high enough concentration to detect small tumors. Use of ICG alone to image hypervascular or "leaky" angiogenic vessels around tumors has been disappointing, due to the dye's limited intrinsic tumor selectivity. Multiple approaches have been employed to improve optical probe localization, including administering it in a quenched form that is activated within tumors, or coupling the fluorescent agents to antibodies or small molecules such as receptor ligands. Recent studies have focused on developing dye conjugates of small bioactive molecules, to improve rapid diffusion to target tissue, incorporate combinatorial and high throughput strategies to identify and optimize new probes, and enhance in vivo stability of the compounds. Some of the peptide and folic-acid analogs of certain ICG derivatives have shown some tumor specificity and are at initial stages of pre-clinical studies.

Recently, a new class of multicarboxylate-containing carbocyanine probes have been reported for use as optical scaffolds that not only serve as fluorescent antennae but also participate in structural assembly of the multivalent molecular construct. The peripheral carboxylic acids that are distal to the chromophore core allow facile conjugation with biomolecules and retain the desirable NIR spectral properties of the dendritic molecule. However, none of these compounds are designed for both tumor detection and therapy. It is important to develop targeting strategies that cope with the heterogeneity of tumors in vivo, where there are inconsistent and varying expression of targeable sites. As discussed below, Photodynamic therapy (PDT) is a clinically effective and still evolving locally selective therapy for cancers. PDT's utility has been demonstrated for varying photosensitizers and multiple types of disease. It is FDA approved for early and late stage lung cancer, obstructive esophageal cancer, high-grade dysplasia associated with Barrett's esophagus, age-related macular degeneration and actinic keratoses. PDT employs tumor localizing photosensitizers that produce reactive singlet oxygen upon absorption of light. Subsequent oxidation-reduction reactions also can produce superoxide anions, hydrogen peroxide and hydroxyl radicals. Photosensitizers have been designed which localize relatively specifically in certain subcellular structures such as the mitochondria, which are exquisitely sensitive targets. On the tumor tissue level, direct photodynamic tumor cell kill, destruction of the tumor supporting vasculature and possibly activation of the innate and adaptive anti-tumor immune system interact to destroy the malignant tissue. The preferential killing of the targeted cells (e.g. tumor), rather than adjacent normal tissues, is essential for PDT, and the preferential target damage achieved in clinical applications is a major driving force behind the use of the modality. The success of PDT relies on development of tumor-avid molecules that are preferentially retained in malignant cells but cleared from normal tissues.

Clinical PDT initially was developed at Roswell Park Cancer Institute which has one of the world's largest basic and clinical research programs. Initially the RPCI group developed Photofrin®, the first generation FDA approved hematoporphyrin-based compound. Subsequently, our group has investigated the structure activity relationships for tumor selectivity and photosensitizing efficacy, and used the information to design new photosensitizers with high selectivity and desirable pharmacokinetics. Although the mechanism of porphyrin retention by tumors in not well understood, the balance between lipophilicity and hydrophilicity is recognized as an important factor. In efforts to develop effective photosensitizers with the required photophysical characteristics, chlorophyll-a and bacteriochlorophyll-a were as the substrates. An extensive QSAR study on a series of the alkyl ether derivatives of pyropheophorbide-a (660 nm) led to selection of the best candidate, HPPH (hexyl ether derivative), [98, 99] currently in promising Phase II clinical trials. Our PS development currently is being extended in purpurinimide (700 nm) and bacteriopurpurinimde (780-800 nm) series with high singlet oxygen ($^1O_2$) producing capability. The long wavelength absorption is important for treating large deep-seated tumors, because it both increases light penetration and minimizes the number of optical fibers needed for light delivery within the tumor.

Some of these compounds are highly tumor avid. As shown in FIG. 18 in the Preliminary Data, with an optimized system, 48 and 72 h after administration, ratios of ~6:1 and 10:1 between the tumor and surrounding muscle and other body sites have been achieved, except for the liver, spleen and kidney. This in vivo selectivity is 2-3 fold greater than that reported for a carbocyanine dye coupled to a somatostatin analog.

Photosensitizers (PS), especially tetrapyrollic photosensitizers such as porphyrins, are not optimal for tumor detection. Examples of such tetrapyrollic photosensitizers are intended to include modified chlorines, bacteriochlorins, hematoporphyrins, porphyrins, purpurins, purpurin imides, and pyropheophorbides. All of the foregoing are referred to herein as porphyrins. Examples of such photodynamic compounds are described in numerous patents in this area that have been applied for and granted world wide on these photodynamic compounds. Reference may be had, for example to the following U.S. Patents which are incorporated herein by reference: U.S. Pat. Nos. 4,649,151; 4,866,168; 4,889,129; 4,932,934; 4,968,715; 5,002,962; 5,015,463; 5,028,621; 5,145,863; 5,198,460; 5,225,433; 5,314,905; 5,459,159; 5,498,710; and 5,591,847.

Such photosensitizers generally fluoresce and the fluorescence properties of these porphyrins in vivo has been exploited by several investigators for the detection of early-stage cancers in the lung, bladder and various other sites. In addition, for treatment of early disease or for deep seated tumors the fluorescence can be used to guide the activating light. However, such photosensitizers are not optimal fluorophores for tumor detection for several reasons: (i) They have low quantum yields. Because the excited state energy is transferred to the triplet state and then to molecular oxygen, efficient photosensitizers tend to have lower fluorescence efficiency (quantum yield) than compounds designed to be fluorophores, such as cyanine dyes. (ii) They have small Stokes shifts. Porphyrin-based photosensitizers have a relatively small difference between the long wavelength absorption band and the fluorescence wavelength (Stokes shift), which makes it technically difficult to separate the fluorescence from the excitation wavelength. (iii) They have relatively short fluorescent wavelengths, <800 nm, which are not optimal for deep tissue penetration.

Bifunctional photosensitizer-flurophore conjugates can optimize tumor detection and treatment. Certain bifunctional conjugates have been recently developed that use tumor-avid photo sensitizers to target the NIR fluorophores to the tumor. The function of the fluorophore is to visualize the tumor location and treatment site. The presence of the photosensitizer allows subsequent tumor ablation. A compound that effectively functions both as a fluorescence imaging agent and a photosensitizer would create an entirely new paradigm for tumor detection and therapy. The optical imaging allows the clinician performing photodynamic therapy to continuously acquire and display patient data in real-time. This "see and treat" approach may determine where to treat superficial carcinomas and how to reach deep-seated tumors in sites such as the breast with optical fibers delivering the photoactivating light.

Metallized photodynamic compounds have shown promise in in vivo PDT efficacy and fluorescence imaging potential. However, the therapeutic dose was significantly higher than the therapeutic dose and a considerable fluorescence resonance energy transfer (FRET) was observed between the two chromophores.

BRIEF SUMMARY OF THE INVENTION

We used two approaches to solve the above problems.
(i) To introduce those metals in the photosensitizers, which are known for enhancing the singlet oxygen yields, and
(ii) to link the chromophores with variable linkers (flexible or rigid) and investigate the effect of the length of linkers in FRET its correlation with PDT.

In particular, we prepared a novel compound in the form of a metallized tetrpyrollic photosensizer linked to a fluorescent dye.

Compounds of the invention have the general formula:

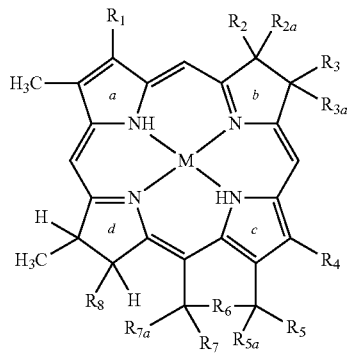

where
$R_1$ is, substituted or unsubstituted, $-CH=CH_2$, $-CHO$, $-COOH$, or

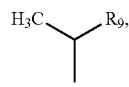

where $R_9=-OR_{10}$ where $R_{10}$ is lower alkyl of 1 through 8 carbon atoms, or $-(CH_2-O)_nCH_3$; $R_2$, $R_{2a}$, $R_3$, $R_{3a}$, $R_4$, $R_5$, $R_{5a}$, $R_7$, and $R_{7a}$ are independently hydrogen, lower alkyl, substituted lower alkyl, lower alkylene or substituted lower alkylene or two $R_2$, $R_{2a}$, $R_3$, and $R_{3a}$ groups on adjacent carbon atoms may be taken together to form a covalent bond or two $R_2$, $R_{2a}$, $R_3$, $R_{3a}$, $R_5$, $R_{5a}$, $R_7$, and $R_{7a}$ groups on the same carbon atom may form a double bond to a divalent pendant group; $R_2$ and $R_3$ may together form a 5 or 6 membered heterocyclic ring containing oxygen, nitrogen or sulfur; $R_6$ is $-CH_2-$, $-NR_{11}-$, where $R_{11}$ is, substituted or unsubstituted, lower alkyl, or lower alkylene; or a $R_6$ is a covalent bond; $R_8$ is $-(CH_2)_2CO_2R_{12}$ where $R_{12}$ is a non-toxic fluorescent dye group that causes the conjugate to preferentially emit (fluoresce) at a wave length of 800 to about 900 nm and M is In, Ga or Pd.

DETAILED DESCRIPTION OF THE INVENTION

The compound in accordance with the invention is a photosensitizer (PS), linked by essentially any structure that does not have detrimental radiation emmitance or absorbing characteristics, to a fluorophore, usually a cyanine dye (CD). The photosensitizer in accordance the invention is a metallized analog of porphyrins, chlorins, purpurinimides, bacterio pupurinimides, phthalocyanines, expanded porphyrins, benzoporphyrin derivatives and purpurins.

The fluorophore is usually a cyanine dye with variable substituents.

Structures, photophysical, tumor-imaging characteristics and in vivo efficacy of the metallated analogs of the HPPH-Cyanine dye conjugates:

Indium, Gallium and Palladium Analogs of HPPH-Cyanine Dye Conjugate:

HPPH-CD Conjugate

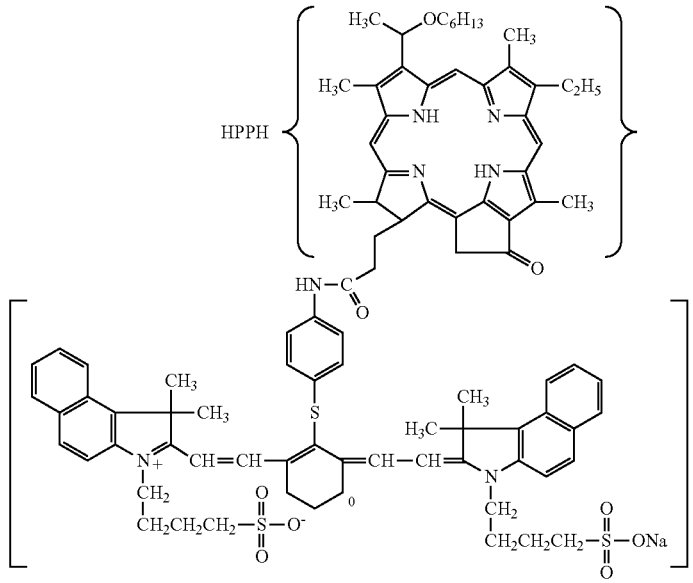

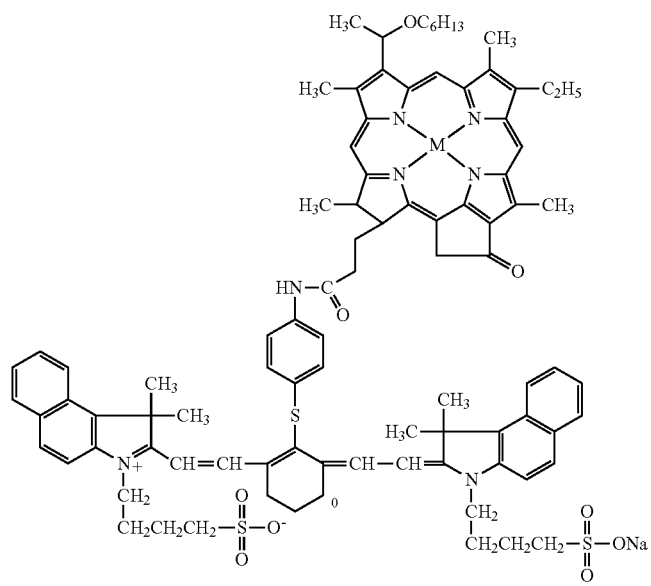
762: M = In
776: M = Ga
777: M = Pd
HPPH-CD Linked with Variable Length of Carbon Linkages:
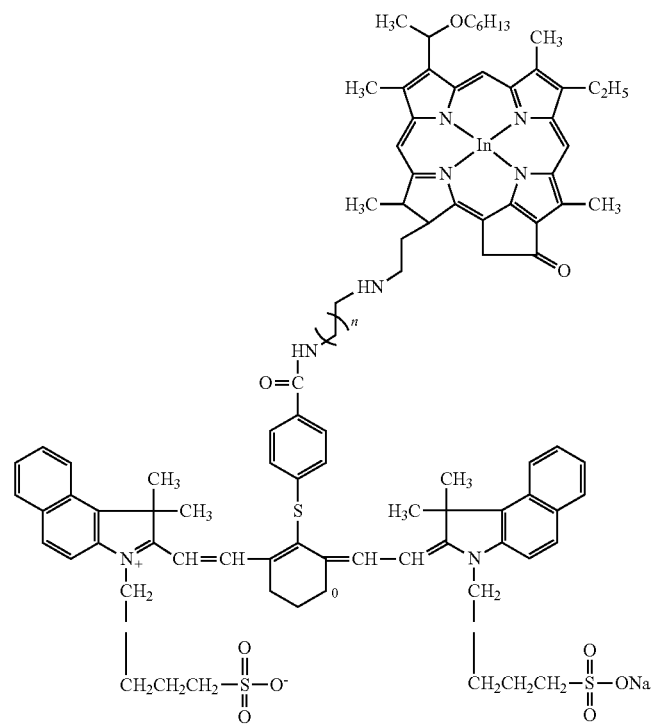
731. n = 3
771. n = 6

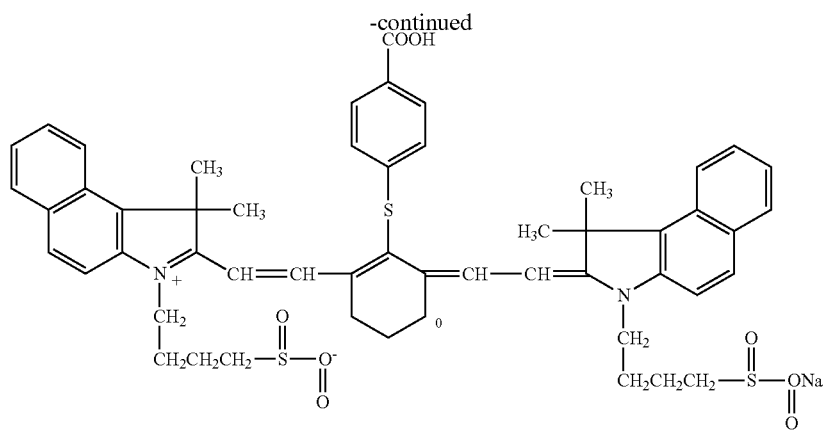

Figure 1:
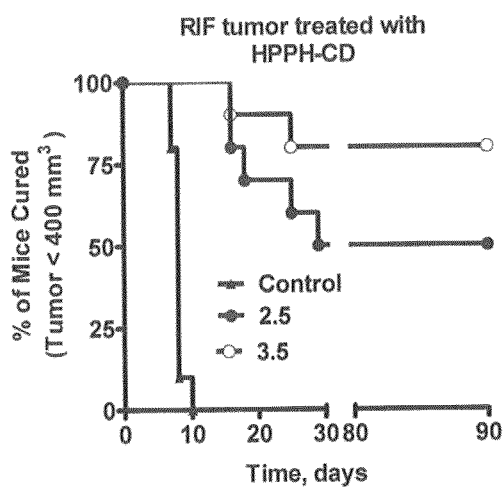
FIG. 1 is a graph showing results of treatment of tumors in mice with HPPH-cyanine dye (CD) conjugate in different concentrations.
Figure 2:
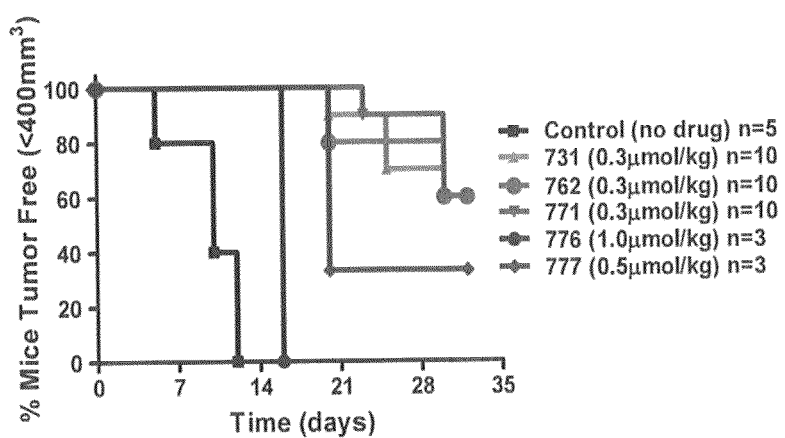
FIG. 2 is a graph showing results of treatment of tumors in mice with metal chelates of HPPH-cyanine dye (CD) conjugates.

Insertion of metal (In, Ga and Pd) in HPPH-CD conjugate enhances PDT effects. Among the metallated analogs, the corresponding In(III) analog produced the best efficacy and was almost 8-fold more effective than the non metallated derivative. See FIGS. 1 and 2.

Figure 3:
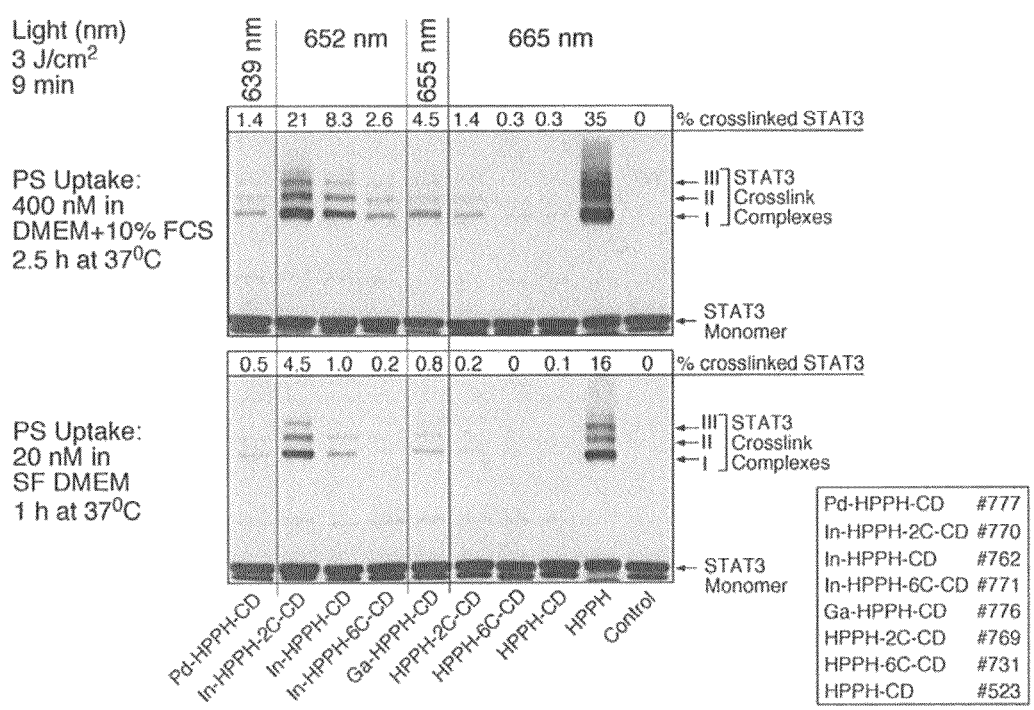
FIG. 3 shows electrophoresis gels of relative proportions of STAT-3 dimers and STAT-3 monomers after treatment with compounds of the invention.

STAT-3 dimerization can be used as biomarker to monitor the PDT response. As seen in FIG. 3, photoreactions mediated by HPPH-CD and metallated derivatives. BCC1 cells were used for determining the level of photoreaction resulting in the oxidative crosslinking of STAT3. The uptake of the compounds was carried out under two conditions. The HPPH derivatives were diluted to 400 nM in culture medium containing 10% fetal calf serum and added to subconfluent monolayer cultures of human basal cell carcinoma (BCC-1) cells. The cells were incubated for 2.5 hours at 37° C. Alternatively, the HPPH-derivatives were diluted to 20 nM in serum-free medium and added to BCC-1 cells that had been preincubated for 1.5 hours in serum-free medium. The cells were incubated for 1 hour at 37° C. Following uptake, the cells were washed 3 times with serum-free medium and exposed at 37° C. for 9 min to light at the indicated wavelength. In each case, the total fluence was 3 J/cm$^2$. Cells were immediately extracted with RIPA buffer. Aliquots of the lysates containing 20 μg protein were analyzed by western blotting for the level of STAT3 proteins (one representative exposure of the immunoblots is reproduced). The enhanced chemiluminescence signals for STAT3 monomeric and crosslinked STAT3 were quantified and the relative amount of crosslinked dimeric STAT3 was expressed as percentage of the total STAT3 signal (indicated above each lane in the figure).

Figure 4:
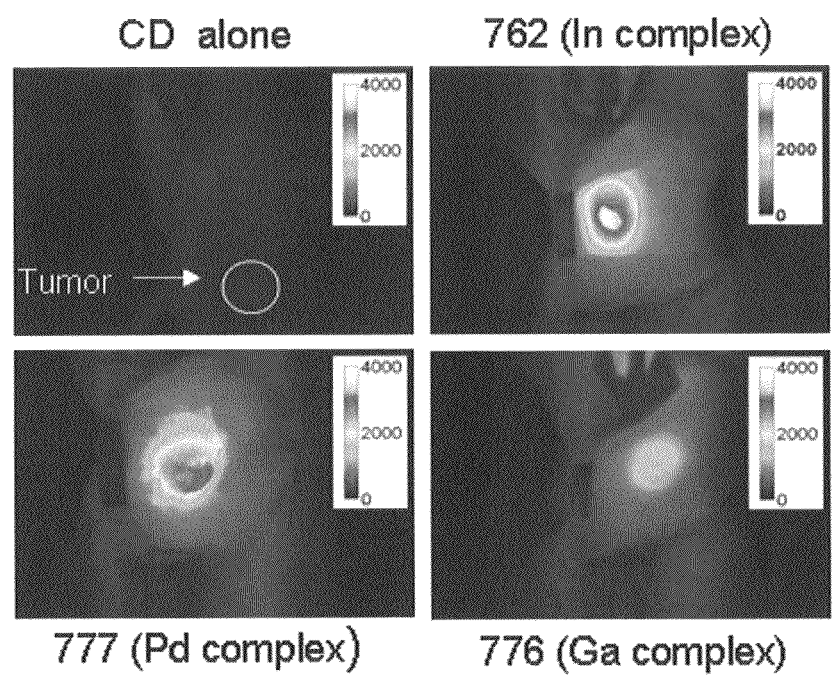
FIG. 4 shows fluorescence images of tumors with HPPH-CD alone compared with complexes of In, Ga, and Pd.

As seen in FIG. 4, in contrast to HPPH-CD where the therapeutic dose was almost 10-fold higher than the tumor-imaging dose. The metallated analogs showed a great potential for PDT and tumor-imaging at the same dose, which was almost 8-fold lower than the therapeutic dose of HPPH-cyanine dye.

The Synthesis of Compound Code No. 762:

HPPH-Cyanine dye conjugate (100 mg), indium chloride (300 mg) and sodium bicarbonate (600 mg) were put in the solvent mixture of toluene (60 ml) and ethanol (20 ml). The reaction mixture was refluxed for 1 hour. After evaporation, the residue was purified by chromatography using MeOH/CH$_2$Cl$_2$ (1:4) as the elute solvent and the title compound was obtained in ~80% yield. UV-vis in MeOH: 835 nm (ε=159430), 646 nm (ε=56500), 602 nm (ε=12425), 563 nm (ε=8762), 416 nm (ε=75074). NMR (CHCl$_3$), δ (ppm) for compound 762: 9.87 (ss looks like a doublet, 1H, meso-H in HPPH part), 9.70 (s, 1H, meso-H in HPPH part), 8.39 (s, 1H, meso-H in HPPH part), 7.98 (m, 4H, aromatic-H of cyanine dye), 7.84 (br s, 4H, aromatic-H of cyanine dye), 7.50 (br s, 4H, aromatic-H of cyanine dye), 7.37 (br s, 4H, =CH— of cyanine dye), 7.07 (m, 4H, 4H of the linker phenyl group), 5.78 (m, 1H, H-3$^1$), 5.17 (m, 1H, H-17), 5.03 (m, 1H, H-18), 4.60 (m, 2H, H-13$^2$), 4.40 (m, 2H, N$^+$—CH$_2$), 4.01 (br, 10H, 2H for N—CH$_2$, 2H for H-17$^1$, 4H for —CH$_2$SO$_3$, 2H for —OC*H$_2$(CH$_2$)$_4$CH$_3$), 3.78 (s, 3H, 7-CH$_3$), 3.59 (s, 3H, 12-CH$_3$), 3.68-3.45 (m, 6H, 4H for SO$_3$—CH$_2$C*H$_2$—(CH$_2$)$_2$, 2H for 8-C*H$_2$CH$_3$), 3.34, (m, 2H, H-17$^2$), 3.31 (s, 3H, 2-CH$_3$), 3.12 (m, 4H, SO$_3$—(CH$_2$)$_2$C*H$_2$—CH$_2$), 2.04 (m, 11H, 3H for 3-CH$_3$, 2H for —OCH$_2$C*H$_2$(CH$_2$)$_3$CH$_3$), 1.73 (s, 12H, 4X—CH$_3$ of cyanine dye), 1.33 (m, 3H, 18-CH$_3$), 1.26 (m, 3H, 8-CH$_2$C*H$_3$), 1.15 (in, 6H, —O(CH$_2$)$_2$(C*H$_2$)$_3$CH$_3$), 0.71 (m, 3H, —O(CH$_2$)$_5$C*H$_3$). MS for 762: Calculated for C$_{91}$H$_{102}$N$_7$O$_9$S$_3$InCl: 1682.6, Found: 1682.5.

The Synthesis of Compound Ga(Cl)-776:

HPPH-CD (100 mg), gallium chloride (400 mg) and sodium bicarbonate (400 mg) were put in the solvent mixture of toluene (65 ml) and ethanol (25 ml). The reaction mixture was refluxed for 30 minutes. After evaporation, the residue was purified by chromatography using MeOH/CH$_2$Cl$_2$ (1:4) as the elute solvent and the title compound was obtained in ~45% yield. UV-vis in MeOH: 839 nm (ε=159183), 649 nm (ε=55102), 606 nm (ε=12505), 563 nm (ε=8767), 419 nm (ε=144002). NMR (CHCl$_3$), δ (ppm) for compound 776: 9.70 (s, 1H, meso-H in HPPH part), 9.22 (s, 1H, meso-H in HPPH part), 8.64 (s, 1H, meso-H in HPPH part), 8.12 (m, 4H, aromatic-H of cyanine dye), 8.02 (br s, 4H, aromatic-H of cyanine dye), 7.73 (br s, 4H, aromatic-H of cyanine dye), 7.46 (br s, 4H, =CH— of cyanine dye), 7.18 (m, 4H, 4H of the linker phenyl group), 5.79 (m, 1H, H-3$^1$), 5.19 (m, 1H, H-17), 5.01 (m, 1H, H-18), 4.63 (m, 2H, H-13$^2$), 4.45 (m, 2H, N$^+$—CH$_2$), 4.07 (br, 10H, 2H for N—CH$_2$, 2H for H-17$^1$, 4H for —CH$_2$SO$_3$, 2H for —OC*H$_2$(CH$_2$)$_4$CH$_3$), 3.79 (s, 3H, 7-CH$_3$), 3.55 (s, 3H, 12-CH$_3$), 3.69-3.44 (m, 6H, 4H for SO$_3$—CH$_2$C*H$_2$—(CH$_2$)$_2$, 2H for 8-C*H$_2$CH$_3$), 3.32, (m, 2H, H-17$^2$), 3.36 (s, 3H, 2-CH$_3$), 3.12 (m, 4H, SO$_3$—(CH$_2$)$_2$C*H$_2$—CH$_2$), 2.02 (m, 11H, 3H for 3-CH$_3$, 2H for —OCH$_2$C*H$_2$(CH$_2$)$_3$CH$_3$), 1.75 (s, 12H, 4X—CH$_3$ of cyanine dye), 1.31 (m, 3H, 18-CH$_3$), 1.24 (m, 3H, 8-CH$_2$C*H$_3$), 1.17 (m, 6H, —O(CH$_2$)$_2$(C*H$_2$)$_3$CH$_3$), 0.73 (m, 3H, —O(CH$_2$)$_5$C*H$_3$). MS for 776: Calculated for C$_{91}$H$_{102}$N$_7$O$_9$S$_3$GaCl: 1636.6, Found: 1636.1.

The Synthesis of Compound 777:

HPPH-Cyanine dye (100 mg), L-ascorbic acid 6-palmitate (220 mg), and palladium acetate (160 mg) were put into the solvent mixture of methanol (80 ml) and chloroform (80 ml). Under argon the reaction mixture was stirred overnight at room temperature. After work-up and evaporation, the residue was purified by chromatography using MeOH/CH$_2$Cl$_2$ (1:5) as the elute solvent and the title compound was obtained in ~85% yield. UV-vis in MeOH: 839 nm (ε=132340), 635 nm (ε=65069), 589 nm (ε=11949), 536 nm (ε=9091), 415 nm (ε=59484), 389.9 nm (ε=62212). NMR (CHCl$_3$), δ (ppm) for compound 777: 9.75 (s, 1H, meso-H in HPPH part), 9.61 (s, 1H, meso-H in HPPH part), 8.45 (s, 1H, meso-H in HPPH part), 7.72 (m, 4H, aromatic-H of cyanine dye), 7.53 (br s, 4H, aromatic-H of cyanine dye), 7.12 (br s, 4H, aromatic-H of cyanine dye), 6.93 (br s, 4H, =CH— of cyanine dye), 6.80 (m, 4H, 4H of the linker phenyl group), 5.64 (m, 1H, H-3$^1$), 5.32 (m, 1H, H-17), 5.02 (m, 1H, H-18), 4.64 (m, 2H, H-13$^2$), 4.47 (m, 2H, N$^+$—CH$_2$), 4.09 (br, 10H, 2H for N—CH$_2$, 2H for H-17$^1$, 4H for —CH$_2$SO$_3$, 2H for —OC*H$_2$(CH$_2$)$_4$CH$_3$), 3.76 (s, 3H, 7-CH$_3$), 3.57 (s, 3H, 12-CH$_3$), 3.67-3.46 (m, 6H, 4H for SO$_3$—CH$_2$C*H$_2$—(CH$_2$)$_2$, 2H for 8-C*H$_2$CH$_3$), 3.35, (m, 2H, H-17$^2$), 3.31 (s, 3H, 2-CH$_3$), 3.16 (m, 4H, SO$_3$—(CH$_2$)$_2$C*H$_2$—CH$_2$), 2.05 (m, 11H, 3H for 3-CH$_3$, 2H for —OCH$_2$C*H$_2$(CH$_2$)$_3$CH$_3$), 1.73 (s, 12H, 4X—CH$_3$ of cyanine dye), 1.34 (m, 3H, 18-CH$_3$), 1.21 (m, 3H, 8-CH$_2$C*H$_3$), 1.15 (m, 6H, —O(CH$_2$)$_2$(C*H$_2$)$_3$CH$_3$), 0.71 (m, 3H, —O(CH$_2$)$_5$C*H$_3$). MS for 777: Calculated for C$_{91}$H$_{102}$N$_7$O$_9$S$_3$Pd: 1638.6, Found: 1638.5.

Amino Diethyl Analog of HPPH:

HPPH (100.0 mg, 0.157 mmol) was taken in a dry RBF (50.0 ml) and dissolved in dry dichloromethane (30.0 ml). To this, N—BOC-ethylenediamine (50.3 mg, 0.314 mmol), N-Ethyl-N'-(3-dimethylaminopropyl) carbodiimide hydrochloride (60.2 mg, 0.314 mmol) and 4-dimethylamino pyridine (38.36 mg, 0.314 mmol) were added and the resultant mixture was stirred for 12 hr at room temperature under N$_2$ atmosphere. Reaction mixture was then diluted with dichloromethane (50.0 ml) and washed with brine (50 ml). Organic layer separated, dried over sodium sulfate and concentrated. Product was purified over silica gel column using 1-3% methanol-dichloromethane as mobile phase. Yield: 105.0 mg (85.9%). UV-vis $\lambda_{max}$(in CH$_2$Cl$_2$): 661 nm ($\alpha$ 5.0×10$^4$), 604 nm ($\epsilon$ 0.8×10$^4$), 537 nm ($\epsilon$ 0.9×10$^4$), 505 nm ($\epsilon$ 0.9×10$^4$), and 410 nm ($\epsilon$ 10.5×10$^4$). $^1$H NMR (400 MHz, CDCl$_3$): δ 9.76 (singlet, 1H, meso-H), 9.21 (singlet, 1H, meso-H), 8.52 (singlet, 1H, meso-H), 6.12 (brs, 1H, NH), 5.92 (m, 1H, CH$_3$C HOhexyl), 5.29 (d, 1H, 15$^1$-C*HH, J=19.6 Hz), 5.09 (d, 1H, T5$^1$-CH*H, J=20.0 Hz), 4.85 (brs, 1H, NH), 4.52 (q, 1H, 17-H, J=7.6 Hz), 4.30 (d, 1H, H-18, J=5.2 Hz), 3.62-3.61 (m, 4H, 8-C*H$_2$CH$_3$ & —OC*H$_2$-Hexyl), 3.38 (singlet, 3H, ring-CH$_3$), 3.28 (singlet, 3H, ring-CH$_3$), 3.28 (singlet, 3H, ring-CH$_3$), 3.18 (in, 2H, —(NHCH$_2$)$_2$—), 3.08 (m, 2H, —(NHCH$_2$)$_2$—), 2.65 (m, 1H, 17$^2$-C*HH), 2.45 (m, 1H, 17$^2$-CH*H), 2.30 (m, 1H, 17$^1$-C*HH), 2.13 (d, 3H, C*H$_3$CH—Ohexyl, J=7.2 Hz), 2.05 (m, 1H, 17$^1$-C*HH), 1.80 (d, 3H, 18-CH$_3$, J=7.2 Hz), 1.75 (m, 2H, —CH$_2$-Hexyl), 1.63 (t, 3H, 8-CH$_2$C*H$_3$, J=7.2 Hz), 1.43 (m, 2H, —CH$_2$-Hexyl), 1.24 (m, 4H, -2CH$_2$-Hexyl), 1.21 (s, 9H, NH-Boc), 0.80 (t, 3H, CH$_3$-Hexyl, J=6.8 Hz), 0.45 (brs, 1H, NH), −1.65 (brs, 1H, NH). MS calculated for C$_{46}$H$_{62}$N$_6$O$_5$ 779.02. EIMS: 779.3 (M$^+$).

Aminohexane Analog of HPPH:

HPPH (100.0 mg, 0.157 mmol) was taken in a dry RBF (50.0 ml) and dissolved in dry dichloromethane (30.0 ml). To this, N—BOC-1,6 diaminohexane (60.0 mg, 0.31 mmol), N-Ethyl-N'-(3-dimethylaminopropyl) carbodiimide hydrochloride (70.0 mg, 0.31 mmol) and 4-dimethylamino pyridine (38.36 mg, 0.314 mmol) were added and the resultant mixture was stirred for 12 hr at room temperature under N$_2$ atmosphere. Reaction mixture was then diluted with dichloromethane (50.0 ml) and washed with brine (50 ml). Organic layer separated, dried over sodium sulfate and concentrated. Product was purified over silica gel column using 1-3% methanol-dichloromethane as mobile phase. Yield: 105.0 mg (85.9%). UV-vis $\lambda_{max}$ (in CH$_2$Cl$_2$): 661 nm ($\epsilon$ 5.0×10$^4$), 604 nm ($\epsilon$ 0.8×10$^4$), 537 nm ($\epsilon$ 0.9×10$^4$), 505 nm ($\epsilon$ 0.9×10$^4$), and 410 nm ($\epsilon$ 10.5×10$^4$). $^1$H NMR (400 MHz, CDCl$_3$): δ 9.76 (singlet, 1H, meso-H), 9.15 (singlet, 1H, meso-H), 8.50 (singlet, 1H, meso-H), 5.92 (m, 1H, CH$_3$C*HOhexyl), 5.20 (d, 1H, 15$^1$-C*HH, J=19.6 Hz), 5.09 (d, 1H, 15$^1$-CH*H, J=20.0 Hz), 4.52 (q, 1H, 17-H, J=7.6 Hz), 4.30 (d, 1H, H-18, J=5.2 Hz), 3.62-3.61 (m, 4H, 8-C*H$_2$CH$_3$ & —OC*H$_2$-Hexyl), 3.38 (singlet, 3H, ring-CH$_3$), 3.28 (singlet, 3H, ring-CH$_3$), 3.28 (singlet, 3H, ring-CH$_3$), 3.18 (m, 2H, —(NHCH$_2$)$_2$—), 3.08 (m, 2H, —(NHCH$_2$)$_2$—), 2.65 (m, 1H, 17$^2$-CHH), 2.45 (m, 1H, 17$^2$-CH*H), 2.30 (m, 1H, 17$^1$-C*HH), 2.13 (d, 3H, C*H$_3$CH—Ohexyl, J=7.2 Hz), 1.95 (m, 1H, 17$^1$-C*HH), 1.80 (d, 3H, 18-CH$_3$, J=7.2 Hz), 1.75 (m, 2H, —CH$_2$-Hexyl), 1.63 (t, 3H, 8-CH$_2$CH$_3$, J=7.2 Hz), 1.43 (m, 2H, —CH$_2$—Hexyl), 1.40-1.31 (m, 8H, —(NH CH$_2$CH$_2$CH$_2$CH$_2$CH$_2$CH$_2$NH), 1.24 (m, 4H, 2CH$_2$-Hexyl), 1.21 (s, 9H, NH-Boc), 0.80 (t, 3H, CH$_3$-Hexyl, J=6.8 Hz), 0.45 (brs, 1H, NH), −1.65 (brs, 1H, NH). MS calculated for C$_{50}$H$_{70}$N$_6$O$_5$ 835.13 EIMS: 835.8 (M$^+$).

HPPH-Cyanine Dye Joined with a Short Linker (without any Metal):

HPPH-N-Boc ethylenediamine (35.0 mg, 0.052 mmol) was taken in a dry RBF (50.0 ml) and stirred with 50% TFA/DCM (5.0 ml) at RT for 3 hr. Resultant mixture was concentrated and dried under high vacuum to remove trace of TFA. The crude thus obtained was dissolved in anhy. DMF (25 ml) and cyanine dye (50.0 mg, 0.052 mmol), BOP (30.0 mg, 0.067 mmol) and triethyl amine (3-4 drops) were added and the resultant mixture was stirred for 12 hr at room temperature under N$_2$ atmosphere. Solvent was removed under vacuum and the product was purified over preparative plates using 15% methanol-dichloromethane to yield the compound in 35% yield. UV-vis $\lambda_{max}$ (in MeOH): 838.9 nm ($\epsilon$ 2.04× 10$^5$), 659.9 nm ($\epsilon$ 5.13×10$^4$), 607.0 nm ($\epsilon$ 1.16×10$^4$), 538 nm ($\epsilon$ 1.0×10$^4$), 408 nm ($\epsilon$ 8.1×10$^4$) $^1$H NMR (400 Mhz, CD$_3$OD): 9.73 (s, 1H, H-5 of HPPH part), 9.35 (s, 1H, H-10 of HPPH part), 8.50-8.45 (m, 2H, aromatic protons of cyanine dye part), 8.40 (s, 1H, H-20 of HPPH part), 7.73-7.67 (m, 4H, aromatic protons of cyanine dye part), 7.65-7.62 (m, 2H), 7.44-7.42 (m, 2H), 7.37-7.21 (m, 6H), 7.14-7.11 (m, 2H), 6.76-6.74 (d, 2H), 5.91-5.90 (m, 1H, 3$^1$-H of HPPH part), 5.07-5.07 (m, 18-H of HPPH part), 5.02-4.99 (m, 17-H of HPPH part), 4.26 (d, 1H, 13 C*HH of HPPH part), 3.92 (d, 2H, 13 CH*H of HPPH part), 3.62-3.54 (m, 6H, 2H for —NC*H$_2$(CH$_2$)$_3$SO$_3^-$, and 2H for —NC*H$_2$(CH$_2$)$_3$SO$_3^-$ and 2H for 8-C*H$_2$CH$_3$), 3.45-3.44 (overlapped, 6H, 2H for 3$^1$-OC*H$_2$(CH$_2$)$_4$CH$_3$ of HPPH part, 4H for 2X—N(CH$_2$)$_3$C*H$_2$SO$_3^-$), 3.33 (s, 3H, 7-CH$_3$ of HPPH), 3.31 (s, 3H, 2-CH$_3$), 3.19 (s, 3H, 12-CH$_3$), 2.83-2.81 (m, 2H for 17-CH$_2$C*H$_2$CO—), 2.68-2.63 (m, 12H, 8H for 2X—NCH$_2$(C*H$_2$)$_2$CH$_2$SO$_3^-$ of cyanine dye part, 4H for —CONHC*H$_2$C*H$_2$NHCO—), 2.43-2.63 (m, 2H for 17-C*H$_2$CH$_2$CO—), 2.10-2.10 (overlapped with other peaks, 3H, 3$^2$-CH$_3$ of HPPH part), 1.65-1.57 (m, 6H, cyclohexene-(CH$_2$)$_3$— of cyanine dye part), 1.53-1.50 (m, 3H for 18-CH$_3$), 1.29-1.12 (overlapped, 17H, 12H for 4X—CH$_3$ of cyanine dye part, 2H for 3$^1$-OCH$_2$C*H$_2$(CH$_2$)$_3$CH$_3$ of HPPH part, 3H for 8-CH$_2$C*H$_3$ of HPPH part), 1.17-1.14 (m, 6H for 3$^1$-O(CH$_2$)$_2$(C*H$_2$)$_3$CH$_3$), 0.66 (m, 3H for 3$^1$-OCH$_2$(CH$_2$)$_4$C*H$_3$). MS calculated for C$_{94}$H$_{108}$N$_8$O$_{10}$S$_3$ 1628 EIMS (m/z): 1650 (M$^+$+Na).

Synthesis of HPPH-CD Linked with a Long, without any Metal):

HPPH-N-Boc hexyldiamine (38.0 mg, 0.052 mmol) was taken in a dry RBF (50.0 ml) and stirred with 50% TFA/DCM (5.0 ml) at RT for 3 hr. Resultant mixture was concentrated and dried under high vacuum to remove trace of TFA. The crude thus obtained was dissolved in anhy. DMF (25 ml) and cyanine dye (50.0 mg, 0.052 mmol), BOP (30.0 mg, 0.067 mmol) and triethyl amine (3-4 drops) were added and the resultant mixture was stirred for 12 hr at room temperature under N$_2$ atmosphere. Solvent was removed under vacuum and the product was purified over preparative plates using 15% methanol-dichloromethane to yield the compound in 35% yield. UV-vis $\lambda_{max}$ (in MeOH): 838.1 nm ($\epsilon$ 2.23×10$^5$), 661.0 nm ($\epsilon$ 5.34×10$^4$), 609.0 nm ($\epsilon$ 1.02×10$^4$), 538 nm ($\epsilon$ 8.79×10$^4$), 408 nm ($\epsilon$ 9.07×10$^5$) $^1$H NMR (400 MHz, CD$_3$OD): 9.65 (s, 1H, H-5 of HPPH part), 8.93 (s, 1H, H-10 of HPPH part), 8.75-832 (m, 3H, 1H, H-20 of HPPH part, 2H, aromatic protons of cyanine dye part), 7.76 (m, 2H, aromatic protons of cyanine dye part), 7.70-7.67 (m, 4H, aromatic protons of cyanine dye part), 7.46-7.43 (m, 2H), 7.30-7.29

(m, 2H), 7.20-7.19 (m, 4H) 6.87-6.83 (m, 2H), 5.98 (d, 2H), 5.84-5.86 (m, 1H, $3^1$-H of HPPH part), 5.01-4.99 (m, 18-H of HPPH part), 4.80-4.77 (m, 17-H of HPPH part), 4.38 (d, 1H, 13 C*HH of HPPH part), 4.05 (d, 1H, 13 CH*H of HPPH part), 3.70-3.60 (m, 2H, —NC*$H_2(CH_2)_3SO_3^-$), 3.50-3.45 (m, 2H, —NC*$H_2(CH_2)_3SO_3^-$), 3.38-3.35 (overlapped, 5H, 3H of 7-$CH_3$ of HPPH and 2H of 8-C*$H_2CH_3$), 3.33-3.45 (overlapped, 8H-1, 2H for $3^1$-OC*$H_2(CH_2)_4CH_3$ of HPPH part, 3H of 2-$CH_3$ and 3H of 12-$CH_3$), 3.25-3.15 (m, 6H, 2H for 17-$CH_2$C*$H_2$CO— and 4H for 2X—N($CH_2)_3$C*$H_2SO_3$), 2.80-2.65 (m, 12H, 8H for 2X—NC$H_2$(C*$H_2)_2CH_2SO_3^-$ of cyanine dye part, 4H for —CONHC*$H_2(CH_2)_4CH_2$NHCO—), 2.30-2.22 (2H for 17-C*$H_2CH_2$CO), 2.13-2.08 (overlapped with other peaks, 3H, $3^2$-$CH_3$ of HPPH part), 1.75-1.60 (m, 9H, 6H for cyclohexene-(C*$H_2)_3$— of cyanine dye part, and 3H for 18-$CH_3$), 1.49-1.36 (overlapped, 17H, 12H for 4X—$CH_3$ of cyanine dye part, 3H for 8-C$H_2$C*$H_3$ of HPPH part), 2H for $3^1$-OC$H_2$C*$H_2(CH_2)_3CH_3$ of HPPH part), 1.35-1.15 (m, 14H, 6H for $3^1$-O($CH_2)_2$(C*$H_2)_3CH_3$, 8H for —CONHC$H_2$(C*$H_2)_4CH_2$NHCO—), 0.65 (m, 3H for $3^1$-OC$H_2(CH_2)_4$C*$H_3$). MS calculated for $C_{98}H_{116}N_8O_{10}S_3$ 1684 EIMS (m/z): 1706 (M$^+$+Na).

Synthesis of (HPPH-CD Linked with a Long Linker, without) 731:

To a round bottom flask the foregoing conjugate (25 mg) in toluene (50 ml) and DMF (1-2 ml) was added Indium chloride (75 mg) and sodium bicarbonate (150 mg). Mixture was refluxed for 3 hours under argon. The solvent was removed under vacuum and the product was purified over preparative plates using 15% methanol-dichloromethane to yield the compound in 65% yield. UV-vis $\lambda_{max}$ (in MeOH): 836.0 nm ($\epsilon$ 1.91×10$^5$), 646.0 nm ($\epsilon$ 7.55×10$^4$), 602.0 nm ($\epsilon$ 1.20×10$^4$), 564 nm ($\epsilon$ 6.79×10$^4$), 417 nm ($\epsilon$ 9.30×10$^5$) $^1$H NMR (400 Mhz, $CH_3$OD): 10.07 (s, 1H, H-5 of HPPH part), 9.90 (s, 1H, H-10 of HPPH part), 8.75-8.72 (m, 3H, 1H, H-20 of HPPH part, 2H, aromatic protons of cyanine dye part), 8.07 (m, 2H, aromatic protons of cyanine dye part), 7.93-7.89 (m, 4H, aromatic protons of cyanine dye part), 7.55-7.40 (m, 8H), 7.18-7.17 (m, 2H), 6.29 (d, 2H), 5.83-5.80 (m, 1H, $3^1$-H of HPPH part), 5.33-5.28 (m, 18-H of HPPH part), 5.09-5.05 (m, 17-H of HPPH part), 4.25-4.15 (m, 2H, $13^2$-H of HPPH part), 3.90-3.88 (m, 2H, —NC*$H_2(CH_2)_3SO_3^-$), 3.73-3.70 (bs, 5H, 2H for —NC*$H_2(CH_2)_3SO_3^-$, 3H and 7-$CH_3$ of HPPH), 3.61-3.57 (m, 2H, 8-C*$H_2CH_3$), 3.38-3.35 (overlapped, 6H, 2H for $3^1$-OC*$H_2(CH_2)_4CH_3$ of HPPH part, 4H for 2X—N($CH_2)_3$C*$H_2SO_3^-$), 3.40 (s, 6H, 2-$CH_3$ and 12-$CH_3$), 3.34-3.11 (m, 4H for 17-C*$H_2$C*$H_2$CO—), 2.85-2.44 (m, 12H, 8H for 2X—NC$H_2$(C*$H_2)_2CH_2SO_3^-$ of cyanine dye part, 4H for —CONHC*$H_2$C*$H_2$NHCO—), 2.12-2.10 (overlapped with other peaks, 3H, $3^2$-$CH_3$ of HPPH part), 1.90 (m, 6H, cyclohexene-(C*$H_2)_3$— of cyanine dye part), 1.82 (d, 3H for 18-$CH_3$), 1.79-1.72 (overlapped, 17H, 12H for 4X—$CH_3$ of cyanine dye part, 3H for 8-C$H_2$C*$H_3$ of HPPH part, 2H for $3^1$-OC$H_2$C*$H_2(CH_2)_3CH_3$ of HPPH part), 1.33-1.11 (m, 6H for $3^1$-O($CH_2)_2$(C*$H_2)_3CH_3$, 0.71 (t, 3H for $3^1$-OC$H_2(CH_2)_4$C*$H_3$) MS calculated for $C_{94}H_{106}ClInN_8O_{10}S_3$ 1754.36 EIMS (m/z): 1754.7 (M$^+$).

Synthesis of In(III) Complex of HPPH-CD Linked with a Long Linker 771:

To a round bottom flask containing HPPH-CD linked with a long carbon chain (25 mg) in toluene (50 ml) and DMF (1-2 ml) was added Indium chloride (75 mg) and sodium bicarbonate (150 mg). ture was refluxed for 3 hours under argon. The solvent was removed under vacuum and the product was purified over preparative plates using 15% methanol-dichloromethane to yield the compound in 70% yield. UV-vis $\lambda_{max}$ (in MeOH): 836.0 nm ($\epsilon$ 1.98×10$^5$), 646.0 nm ($\epsilon$ 7.33×10$^4$), 602.0 nm ($\epsilon$ 1.24×10$^4$), 565 nm ($\epsilon$ 6.79×10$^4$), 418.1 nm ($\epsilon$ 9.57×10$^5$) $^1$H NMR (400 Mhz, $CH_3$OD): 10.08 (s, 1H, H-5 of HPPH part), 9.91 (s, 1H, H-10 of HPPH part), 8.83-8.75 (m, 3H, 1H, H-20 of HPPH part, 2H, aromatic protons of cyanine dye part), 8.09 (m, 2H, aromatic protons of cyanine dye part), 7.94-7.91 (m, 4H, aromatic protons of cyanine dye part), 7.71-7.66 (2H, protons of cyanine dye part), 7.58-7.50 (m, 4H), 7.43 (t, 2H), 7.35-7.32 (m, 2H), 6.32 (d, 2H), 5.85 (m, 1H, $3^1$-H of HPPH part), 5.29-5.34 (m, 18-H of HPPH part), 5.03 (m, 17-H of HPPH part), 4.26-4.22 (m, 2H, $13^2$-H of HPPH part), 3.92-3.90 (m, 2H, —NC*$H_2(CH_2)_3SO_3^-$), 3.75-3.73 (m, 2H, —NC*$H_2(CH_2)_3SO_3^-$), 3.69 (s, 3H, 7-$CH_3$ of HPPH), 3.63-3.58 (m, 2H, 8-C*$H_2CH_3$), 3.33-3.40 (overlapped, 6H, 2H for $3^1$-OC*$H_2(CH_2)_4CH_3$ of HPPH part, 4H for 2X—N($CH_2)_3$C*$H_2SO_3^-$), 3.40 (s, 3H, 2-$CH_3$), 3.34 (s, 3H, 12-$CH_3$), 3.20-3.18 (m, 2H for 17-C*$H_2CH_2$CO—), 2.94-2.66 (m, 14H, 8H for 2X—NC$H_2$(C*$H_2)_2CH_2SO_3^-$ of cyanine dye part, 2H for 17-$CH_2$C*$H_2$CO—, 4H for —CONHC*$H_2(CH_2)_4$C*$H_2$NHCO—), 2.13-2.08 (overlapped with other peaks, 3H, $3^2$-$CH_3$ of HPPH part), 1.97-1.96 (m, 6H, cyclohexene-(C*$H_2)_3$— of cyanine dye part), 1.88 (d, 3H for 18-$CH_3$), 1.80-1.76 (overlapped, 17H, 12H for 4X—$CH_3$ of cyanine dye part, 3H for 8-C$H_2$C*$H_3$ of HPPH part), 2H for $3^1$-OC$H_2$C*$H_2(CH_2)_3CH_3$ of HPPH part), 1.33-1.11 (m, 14H, 6H for $3^1$-O($CH_2)_2$(C*$H_2)_3CH_3$, 8H for —CONHC$H_2$(C*$H_2)_4CH_2$NHCO—), 0.75-0.70 (m, 3H for $3^1$-OC$H_2(CH_2)_4$C*$H_3$. MS calculated for $C_{98}H_{114}ClInN_8O_{10}S_3$ 1810.4 EIMS (m/z): 1775.5 (M$^+$-Cl).

We claim:

1. A compound in the form of a metallized tetrapyrollic photosensitizer linked to a fluorescent dye.

2. A compound in the form of a metallized tetrapyrollic photosensitizer (PS) linked to a fluorescent dye where the photosensitizer, is linked by essentially any structure that does not have detrimental radiation emittance or absorbing characteristics, to the fluorescent dye.

3. The compound of claim 2 having the formula:

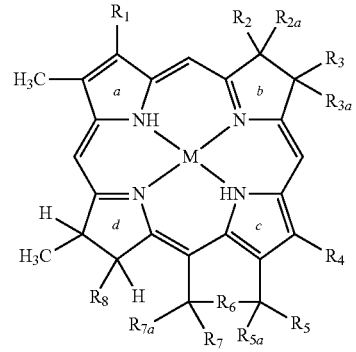

where $R_1$ is, substituted or unsubstituted, —CH=$CH_2$, —CHO, COOH, or

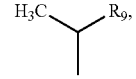

where $R_9$=—$OR_{10}$ where $R_{10}$ is lower alkyl of 1 through 8 carbon atoms, or —($CH_2$—O)$_n$$CH_3$; $R_2$, $R_3$, $R_4$, $R_5$, $R_{5a}$, $R_7$, and $R_{7a}$ are independently hydrogen, lower alkyl, substituted lower alkyl, lower alkylene or substituted lower alkylene, $R_{2a}$ and $R_{3a}$ groups are taken together to form a covalent bond, two, $R_5$, $R_{5a}$, $R_7$, and $R_{7a}$ groups on the same carbon atom may form a double bond to a divalent pendant group; $R_2$ and $R_3$ may together form a 5 or 6 membered heterocyclic ring containing oxygen, nitrogen or sulfur; $R_6$ is —$CH_2$—, —$NR_{11}$—, where $R_{11}$ is, substituted or unsubstituted, lower alkyl, or lower alkylene; or a $R_6$ is a covalent bond; $R_8$ is —($CH_2)_2CO_2R_{12}$ where $R_{12}$ is a non-toxic fluorescent dye group that causes the conjugate to preferentially emit (fluoresce) at a wave length of 800 to about 900 nm and M is In, Ga or Pd.

4. The compound of claim 1 having the formula:

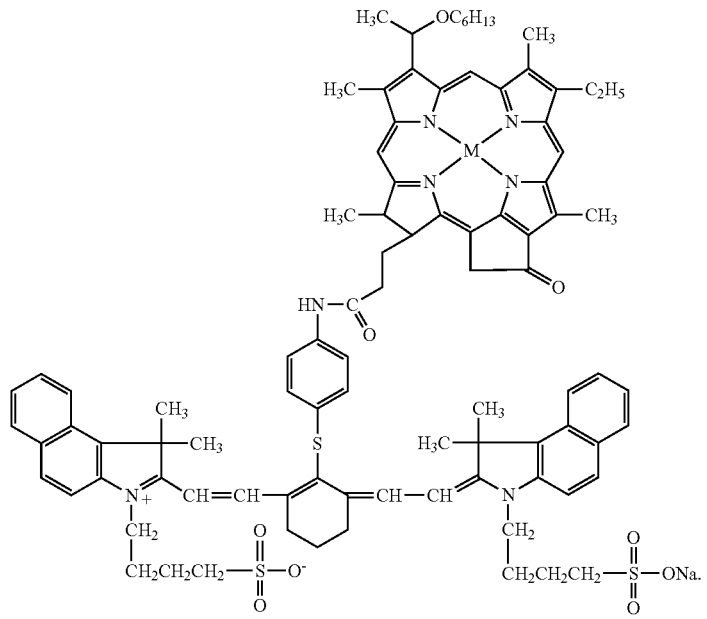

M = In, Ga, Pd, Zn, Ni, Cu

5. The compound of claim 2 where the fluorescent dye is a cyanine dye.

6. The compound of claim 1 where the metallized tetrapyrrollic photosensitizer is an analog of a porphyrin, chlorin, purpurinimide, bacteriopupurinimide, phthalocyanines, expanded porphyrin, benzoporphyrin derivative or purpurin.

* * * * *